US012639848B2

(12) United States Patent
Zhao et al.

(10) Patent No.: US 12,639,848 B2
(45) Date of Patent: May 26, 2026

(54) PIXELWISE POSITIONAL EMBEDDINGS FOR MEDICAL IMAGES IN VISION TRANSFORMERS

(71) Applicant: Siemens Healthineers AG, Forchheim (DE)

(72) Inventors: Gengyan Zhao, Plainsboro, NJ (US); Badhan Kumar Das, Erlangen (DE); Eli Gibson, Plainsboro, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 273 days.

(21) Appl. No.: 18/474,347

(22) Filed: Sep. 26, 2023

(65) Prior Publication Data

US 2025/0104276 A1     Mar. 27, 2025

(51) Int. Cl.
| | |
|---|---|
| *G06K 9/00* | (2022.01) |
| *G06T 7/73* | (2017.01) |
| *G16H 30/40* | (2018.01) |

(52) U.S. Cl.
CPC .............. *G06T 7/74* (2017.01); *G16H 30/40* (2018.01); *G06T 2207/20081* (2013.01); *G06T 2207/20084* (2013.01); *G06T 2207/30016* (2013.01)

(58) Field of Classification Search
CPC ............. G06T 7/74; G06T 2207/20081; G06T 2207/20084; G06T 2207/30016; G16H 30/40; G06V 10/82
See application file for complete search history.

(56) References Cited

U.S. PATENT DOCUMENTS

| | | | | |
|---|---|---|---|---|
| 2017/0164836 A1 * | 6/2017 | Krishnaswamy | .... | A61B 5/0059 |
| 2018/0232883 A1 * | 8/2018 | Sethi | ...................... | G16H 30/40 |
| 2024/0203098 A1 * | 6/2024 | Sultana | .............. | G06V 10/7715 |

FOREIGN PATENT DOCUMENTS

| | | | | | |
|---|---|---|---|---|---|
| KR | 102376249 B1 * | 3/2022 | ............... | G06T 7/11 |
| WO | WO-2010040396 A1 * | 4/2010 | ............... | G06T 5/20 |

OTHER PUBLICATIONS

Extended European Search Report (EESR) mailed Feb. 14, 2025 in corresponding European Patent Application No. 24202841.3.
Xiao Hanguang et al: "Transformers in medical image segmentation: A review", Biomedical Signal Processing and Control, Elsevier, Amsterdam, NL, vol. 84, Mar. 7, 2023.
(Continued)

*Primary Examiner* — Xin Jia

(57) ABSTRACT

Systems and methods for performing a medical imaging analysis task based on pixelwise positionally encoded features are provided. One or more input medical images are received. One or more pixelwise positional embedding images are generated for the one or more input medical images using a spatially varying function. Patches are extracted from the one or more input medical images and the one or more pixelwise positional embedding images. The patches extracted from the one or more input medical images are encoded with corresponding ones of the patches extracted from the one or more pixelwise positional embedding images into pixelwise positionally encoded features. A medical imaging analysis task is performed using a machine learning based network based on the pixelwise positionally encoded features. Results of the medical imaging analysis task are output.

20 Claims, 9 Drawing Sheets

100

Receive one or more input medical images
102

Generate one or more pixelwise positional embedding images for the one or more input medical images using a spatially varying function
104

Extract patches from the one or more input medical images and the one or more pixelwise positional embedding images
106

Encode the patches extracted from the one or more input medical images with corresponding ones of the patches extracted from the one or more pixelwise positional embedding images into pixelwise positionally encoded features
108

Perform a medical imaging analysis task using a machine learning based network based on the pixelwise positionally encoded features
110

Output results of the medical imaging analysis task
112

(56) References Cited

OTHER PUBLICATIONS

Gandhi Dhruvin et al: "A Vision Transformer Approach for Classification an A Small-Sized Medical Image Dataset", 2022 5th International Conference on Advances in Science and Technology (ICAST), IEEE, Dec. 2, 2022 (Dec. 2, 2022), pp. 519-524.

Gai Lulu et al: "Using Vision Transformers in 3-D Medical Image Classifications", 2022 IEEE International Conference on Image Processing (ICIP), IEEE, Oct. 16, 2022 (Oct. 16, 2022), pp. 696-700.

Vaswani et al., "Attention Is All You Need", arXiv:1706.03762, 2017, pp. 1-15.

Dosovitskiy et al., "An Image is Worth 16×16 Words: Transformers for Image Recognition at Scale", arXiv:2010.11929, 2021, pp. 1-22.

Bello et al., "Attention Augmented Convolutional Networks", arXiv:1904.09925v5, 2020, pp. 1-13.

Yang et al., "XLNet: Generalized Autoregressive Pretraining for Language Understanding", arXiv:1906.08237v2, 2020, pp. 1-18.

He et al., "DeBERTa: Decoding-enhanced BERT with Disentangled Attention", arXiv:2006.03654v6, 2021, pp. 1-23.

Hatamizadeh et al., "UNETR: Transformers for 3D Medical Image Segmentation", arXiv:2103.10504v1, 2021, pp. 1-11.

Hatamizadeh et al., "Swin UNETR: Swin Transformers for Semantic Segmentation of Brain Tumors in MRI Images", arXiv:2201.01266v1, 2022, pp. 1-13.

Chen et al., "Transformers Improve Breast Cancer Diagnosis from Unregistered Multi-View Mammograms", Diagnostics, 2022, pp. 1-14.

Mkindu et al., "Lung nodule detection in chest CT images based on vision transformer network with Bayesian optimization", Biomedical Signal Processing and Control, 2023, pp. 1-8.

Chen et al., "TransUNet: Transformers Make Strong Encoders for Medical Image Segmentation", arXiv:2102.04306v1, 2021, pp. 1-13.

Valanarasu et al., "Medical Transformer: Gated Axial-Attention for Medical Image Segmentation", arXiv:2102.10662v2, 2021, pp. 1-18.

Xie et al., "Universal Medical Self-Supervised Learning via Breaking Dimensionality Barrier", arXiv:2112.09356v2, 2022, pp. 1-23.

Ma et al., "Transformer Network for Significant Stenosis Detection in CCTA of Coronary Arteries", arXiv:2107.03035v3, 2021, pp. 1-10.

Simpson et al., "A large annotated medical image dataset for the development and evaluation of segmentation algorithms", arXiv:1902.09063v1, 2019, pp. 1-15.

Liu et al., "Swin Transformer: Hierarchical Vision Transformer using Shifted Windows", arXiv:2103.14030v2, 2021, pp. 1-14.

Wilcoxon, "Individual Comparisons by Ranking Methods", Breakthroughs in Statistics, Biometrics Bulletin, 1945, pp. 80-83.

Isensee et al., "Automated Design of Deep Learning Methods for Biomedical Image Segmentation", arXiv:1904.08128v2, 2020, pp. 1-55.

Ronneberger et al., "U-Net: Convolutional Networks for Biomedical Image Segmentation", arXiv:1505.04597v1, 2015, pp. 1-8.

Futrega et al., "Optimized U-Net for Brain Tumor Segmentation", arXiv:2110.03352v2, 2021, pp. 1-15.

Isensee et al., "nnU-Net: Self-adapting Framework for U-Net-Based Medical Image Segmentation", arXiv:1809.10486v1, 2018, pp. 1-11.

* cited by examiner

FIG. 1

100

```
┌─────────────────────────────────────────────────────────────┐
│              Receive one or more input medical images         │
│                            102                                │
└─────────────────────────────────────────────────────────────┘
                              │
                              ▼
┌─────────────────────────────────────────────────────────────┐
│  Generate one or more pixelwise positional embedding images   │
│  for the one or more input medical images using a spatially   │
│  varying function                                             │
│                            104                                │
└─────────────────────────────────────────────────────────────┘
                              │
                              ▼
┌─────────────────────────────────────────────────────────────┐
│  Extract patches from the one or more input medical images    │
│  and the one or more pixelwise positional embedding images    │
│                            106                                │
└─────────────────────────────────────────────────────────────┘
                              │
                              ▼
┌─────────────────────────────────────────────────────────────┐
│  Encode the patches extracted from the one or more input      │
│  medical images with corresponding ones of the patches        │
│  extracted from the one or more pixelwise positional          │
│  embedding images into pixelwise positionally encoded         │
│  features                                                     │
│                            108                                │
└─────────────────────────────────────────────────────────────┘
                              │
                              ▼
┌─────────────────────────────────────────────────────────────┐
│  Perform a medical imaging analysis task using a machine      │
│  learning based network based on the pixelwise positionally   │
│  encoded features                                             │
│                            110                                │
└─────────────────────────────────────────────────────────────┘
                              │
                              ▼
┌─────────────────────────────────────────────────────────────┐
│       Output results of the medical imaging analysis task     │
│                            112                                │
└─────────────────────────────────────────────────────────────┘
```

FIG. 2
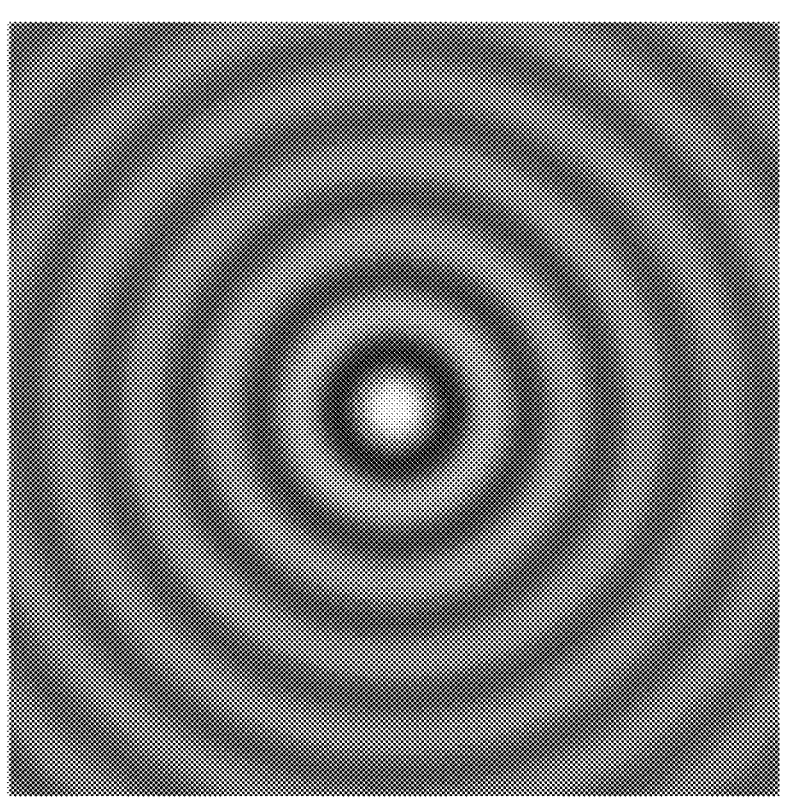

| Vision transformer | Pre-processing | Positional embedding | Dice | True positive HD95 (mm) |
|---|---|---|---|---|
| UNETR | Resample and resize | original | 0.439 | 37.43 |
| | Random crop | original | 0.495 | 36.28 |
| | Random crop | proposed | 0.576* | 27.24 |
| SwinUNETR | Resample and resize | original | 0.537 | 27.94 |
| | Random crop | original | 0.557 | 30.96 |
| | Random crop | proposed | 0.626* | 21.85 |

*Paired Wilcoxon signed rank tests (two-sided); Bonferroni corrected p-value < 0.0001

800

PIXELWISE POSITIONAL EMBEDDINGS FOR MEDICAL IMAGES IN VISION TRANSFORMERS

TECHNICAL FIELD

The present invention relates generally to vision transformers for medical imaging analysis, and in particular to pixelwise positional embeddings for medical images in vision transformers.

BACKGROUND

Vision transformers are a type of neural network for performing various computer vision tasks on input images. Positional embeddings are provided to vision transformers to provide information about the relative or absolute position of patches of the input images. Conventional positional embedding techniques are designed for natural images, which do not inherently capture absolute scale or position, and only embed relative patch-wise positional information of each patch in the input images. Tomographic medical images inherently capture absolute scale and position, which is used to improve comparisons between imaging sessions or between images within an imaging session. However, for clinical and physical reasons, the relationship between image pixels of tomographic medical images and physical coordinates varies between images and are therefore not retained by conventional positional embedding techniques.

BRIEF SUMMARY OF THE INVENTION

In accordance with one or more embodiments, systems, methods, and non-transitory computer readable mediums storing computer program instructions for performing a medical imaging analysis task based on pixelwise positionally encoded features are provided. One or more input medical images are received. One or more pixelwise positional embedding images are generated for the one or more input medical images using a spatially varying function. Patches are extracted from the one or more input medical images and the one or more pixelwise positional embedding images. The patches extracted from the one or more input medical images are encoded with corresponding ones of the patches extracted from the one or more pixelwise positional embedding images into pixelwise positionally encoded features. A medical imaging analysis task is performed using a machine learning based network based on the pixelwise positionally encoded features. Results of the medical imaging analysis task are output.

In one embodiment, generating one or more pixelwise positional embedding images comprises sampling a spatially varying function at a location of each pixel of the one or more input medical images. The spatially varying function may be a sinusoidal function. The spatially varying function may be in reference coordinate system defined relative to the one or more input medical images. The reference coordinate system may comprise a physical coordinate system of an image acquisition device that acquired the one or more input medical images.

In one embodiment, the one or more input medical images comprises a plurality of input medical images and the one or more pixelwise positional embedding images comprises a plurality of pixelwise positional embedding images. Each patch extracted from the plurality of input medical images is combined with its corresponding patch extracted from the plurality of pixelwise positional embedding images. The combined patches are separately encoded.

In one embodiment, the one or more input medical images comprises a plurality of input medical images and the one or more pixelwise positional embedding images comprises a single pixelwise positional embedding image. Corresponding patches extracted from each of the plurality of input medical images and from the single pixelwise positional embedding image are combined. The combined patches are separately encoded.

In one embodiment, the patches extracted from the one or more input medical images are further encoded with patch-wise positionally embedded features to generate patch-wise and pixelwise positionally encoded features. The medical imaging analysis task is performed based on the patch-wise and pixelwise positionally encoded features.

In one embodiment, the machine learning based network is a vision transformer network.

These and other advantages of the invention will be apparent to those of ordinary skill in the art by reference to the following detailed description and the accompanying drawings.

BRIEF DESCRIPTION OF THE DRAWINGS

FIG. 1 shows a method for performing a medical imaging analysis task using a machine learning based network based on pixelwise positional embeddings, in accordance with one or more embodiments;

FIG. 2 shows a pixelwise positional embedding image in two dimensions generated by sampling a 3D spatial sinusoidal function, in accordance with one or more embodiments;

FIG. 6 shows a table comparing performance of embodiments described herein with conventional approaches;

DETAILED DESCRIPTION

Figure 3:
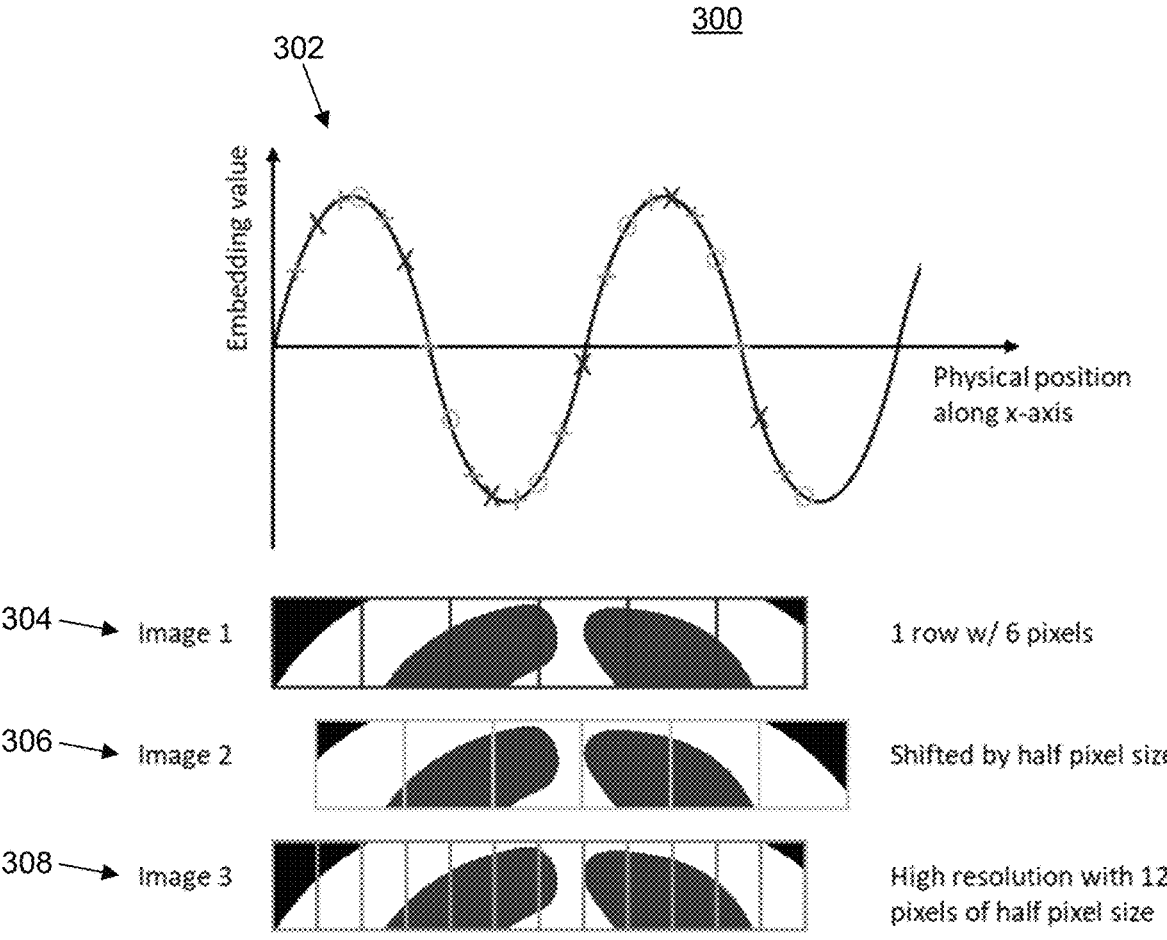
FIG. 3 shows a schematic diagram visually illustrating the calculation of pixelwise positional embedding values, in accordance with one or more embodiments.

The present invention generally relates to methods and systems for utilizing pixelwise positional embeddings for medical images in vision transformers. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/ hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for a vision transformer network for performing a medical imaging analysis task based on pixelwise positional embeddings of one or more input medical images. The pixelwise positional embeddings represent positional information (e.g., origin, pixel spacing, direction, physical extent, size, etc.) determined for each voxel of the one or more input medical images using a spatially varying function. The spatially varying function is defined in a reference coordinate system relative to the one or more input medical images. The pixelwise positional embeddings are represented in pixelwise positional embedding images, which are encoded together with the one or more input medical images into pixelwise positionally encoded features for performing the medical imaging analysis task by the vision transformer network.

Advantageously, embodiments described herein utilize pixelwise positional embeddings, instead of patch-wise positional embeddings utilized in conventional approaches. The pixelwise positional embeddings encode more detailed information of the location, scale, orientation, pixel spacing, field of view, etc. of the one or more input medical images as compared with conventional patch-wise positional information. With the pixelwise positional embeddings, the vision transformer network can extract information more efficiently and learn corresponding positional relationships between pairs of input medical images, thus resulting a better performing vision transformer network. Further, with the pixelwise positional embeddings, the vision transformer network will have the flexibility to take input medical images acquired with different geometry without resampling and the resulting information, which may reduce network performance.

FIG. 1 shows a method 100 for performing a medical imaging analysis task using a machine learning based network based on pixelwise positional embeddings, in accordance with one or more embodiments. The steps of method 100 may be performed by one or more suitable computing devices, such as, e.g., computer 902 of FIG. 9.

At step 102 of FIG. 1, one or more input medical images are received. The one or more input medical images may depict an anatomical object, such as, e.g., organs, vessels, bones, tumors or other abnormalities, or any other anatomical object of interest of a patient. The one or more input medical images may be of any suitable modality, such as, e.g., CT (computed tomography), MRI (magnetic resonance imaging), US (ultrasound), x-ray, or any other medical imaging modality or combinations of medical imaging modalities. The one or more input medical images may be 2D (two-dimensional) images and/or 3D (three-dimensional) volumes.

The one or more input medical images comprise metadata of position information of each pixel, which was recorded by the image acquisition device during acquisition of the one or more input medical images. The position information is defined with respect to a physical coordinate system of the image acquisition device. The position information may comprise, e.g., origin (e.g., the coordinate of the first pixel of the image in the physical coordinate system), pixel spacing (e.g., the pixel size in each dimension of the image matrix), direction (e.g., the affine matrix to map the image matrix index to the coordinate in the physical coordinate system), physical extent (e.g., the field of view of the image), size (e.g., image matrix size), etc. The one or more input medical images are in a medical image format, such as, e.g., DICOM (digital imaging and communications in medicine), MHD (MetaImage MetaHeader), NIFTI (neuroimaging informatics technology initiative), etc., and the metadata may be stored in the header of the one or more input medical images according to the medical image format. Based on the origin and the pixel spacing, the center of each pixel in the physical coordinate system is derived.

Figure 9:
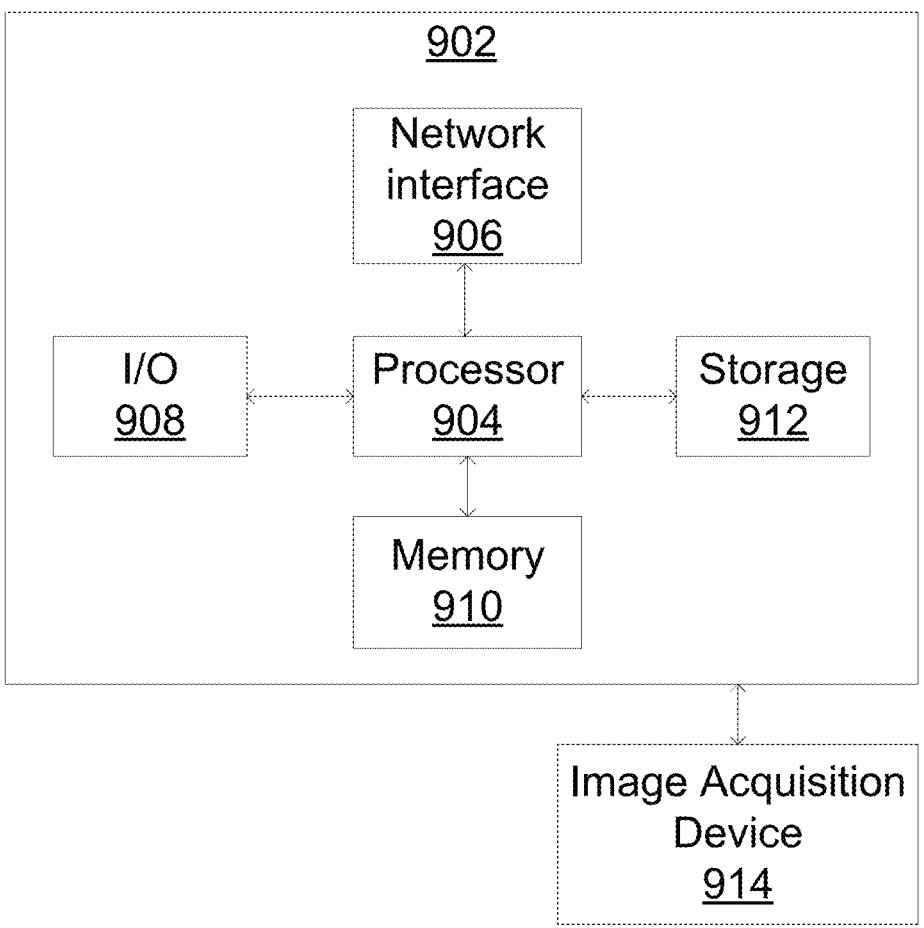
FIG. 9 shows a high-level block diagram of a computer that may be used to implement one or more embodiments.

The one or more input medical images may be received directly from an image acquisition device (e.g., image acquisition device 914 of FIG. 9), such as, e.g., a CT or MRI scanner, as the medical images are acquired, may be received by loading previously acquired medical images from a storage or memory (memory 910 of computer 902 of FIG. 9) of a computer system, or may be received from a remote computer system (e.g., computer 902 of FIG. 9).

At step 104 of FIG. 1, one or more pixelwise positional embedding images are generated for the one or more input medical images using a spatially varying function. In one embodiment, the one or more pixelwise positional embedding images are generated by sampling the spatially varying function at a location of each pixel of the one or more input medical images.

The spatially varying function is defined in a reference coordinate system relative to the one or more input medical images. In one embodiment, the reference coordinate system is the physical coordinate system of the image acquisition device that acquired the one or more input medical images. In another embodiment, the reference coordinate system is defined relative to the one or more input medical images by registering a canonical reference frame to the content of the one or more input medical images by, for example, image-based or landmark-based image registration. In this embodiment, the pixelwise positional embedding values of a pixel depicting a specific anatomical object (e.g., the left retina) would be consistent between imaging sessions, even if the patient is positioned differently. The reference coordinate system may be any other suitable coordinate system.

In one embodiment, the spatially varying function comprises a 3D spatial sinusoidal function defined in the reference coordinate system and centered at the origin of the reference coordinate system. The value at each location of the spatially varying function is a function of the coordinates for that location in the reference coordinate system. One example of a 3D spatial sinusoidal function is Equation (1):

$$f(x, y, z) = A \sin\left(\omega \sqrt{x^2 + y^2 + z^2} + \varphi\right) \qquad (1)$$

FIG. 2 shows a pixelwise positional embedding image 200 in two dimensions generated by sampling the 3D spatial sinusoidal function of Equation (1), in accordance with one or more embodiments. Pixelwise positional embedding image 200 depicts a sinusoidal function having pixelwise positional embedding values calculated according to Equation (1).

Another example of a 3D spatial sinusoidal function is Equation (2):

$$f(x, y, z) = A_x \sin(\omega_x x + \varphi_x) + A_y \sin(\omega_y y + \varphi_y) + A_z \sin(\omega_z z + \varphi_z) \qquad (2)$$

In Equations (1) and (2), hyperparameters A represents the amplitude, ω represents the angular frequency, and φ represents the phase and x, y, and z are coordinates of a pixel. The spatially varying function may comprise any other suitable sinusoidal function or non-sinusoidal function.

The spatially varying function is sampled at the coordinates of the center of each respective pixel of the one or more input medical images in the reference coordinate system to determine pixelwise positional embedding values. For each input medical image, after determining the pixelwise positional embedding values at all pixel center locations, the pixelwise positional embedding values form the embedding image that has the same pixel grid as the input medical image. FIG. 3 shows a schematic diagram 300 visually illustrating the calculation of pixelwise positional embedding values, in accordance with one or more embodiments. Schematic diagram 300 is illustratively shown for one dimension (i.e., the x dimension). Waveform 302 is of a 3D spatial sinusoidal function in the x-dimension depicting the relationship between pixelwise positional embedding values (in the y-axis) and the physical position of the pixel along the x-axis (in the x-axis). Image 1 304 comprises one row with six pixels. Image 2 306 shows the row with six pixels of image 1 304 shifted by half a pixel size. Image 3 308 shows a high-resolution version of image 1 304 comprising 12 pixels of half pixel size. A pixelwise positional embedding value is sampled from waveform 302 for each respective pixel of images 304, 306, and 308 as the value in the y-axis that intersects with the position of the respective pixel along the x-axis in waveform 302. Each pixel of image 1 304 is extracted at the "X" symbol on waveform 302, each pixel of image 2 306 is extracted at the "O" symbol on waveform 302, and each pixel of image 3 308 is extracted at the "+" symbol on waveform 302. Image 1 304, image 2 306, and image 3 308 are acquired with different origins or resolutions, but with the patient at the same position. In this way, the value of the pixelwise positional embeddings reflect the acquisition different of images 302, 304, 306 and their pixels' relative positional relation.

At step 106 of FIG. 1, patches are extracted from the one or more input medical images and the one or more pixelwise positional embedding images. The patches may be extracted by, for example, cropping the one or more input medical images and the one or more pixelwise positional embedding images into a series of nonoverlapping patches with a predefined fixed size.

At step 108 of FIG. 1, the patches extracted from the one or more input medical images are encoded with corresponding ones of the patches extracted from the one or more pixelwise positional embedding images into pixelwise positionally encoded features. A patch extracted from the one or more input medical images and a patch extracted from the one or more pixelwise positional embedding images correspond when they are associated with a same location in the reference coordinate system. The patches may be encoded using any suitable encoder. In one example, the encoder is a machine learning based encoder network (e.g., a CNN, convolutional neural network). In another example, the encoder is a linear projection encoder.

In one embodiment, for example where the one or more input medical images is a single input medical image and the one or more pixelwise positional embedding images is a single pixelwise positional embedding image, each patch extracted from the single input medica image is combined (e.g., added to or concatenated in the channel dimension) with its corresponding patch extracted from the single pixelwise positional embedding image and each combined patch is separately encoded by the encoder.

Figure 4:
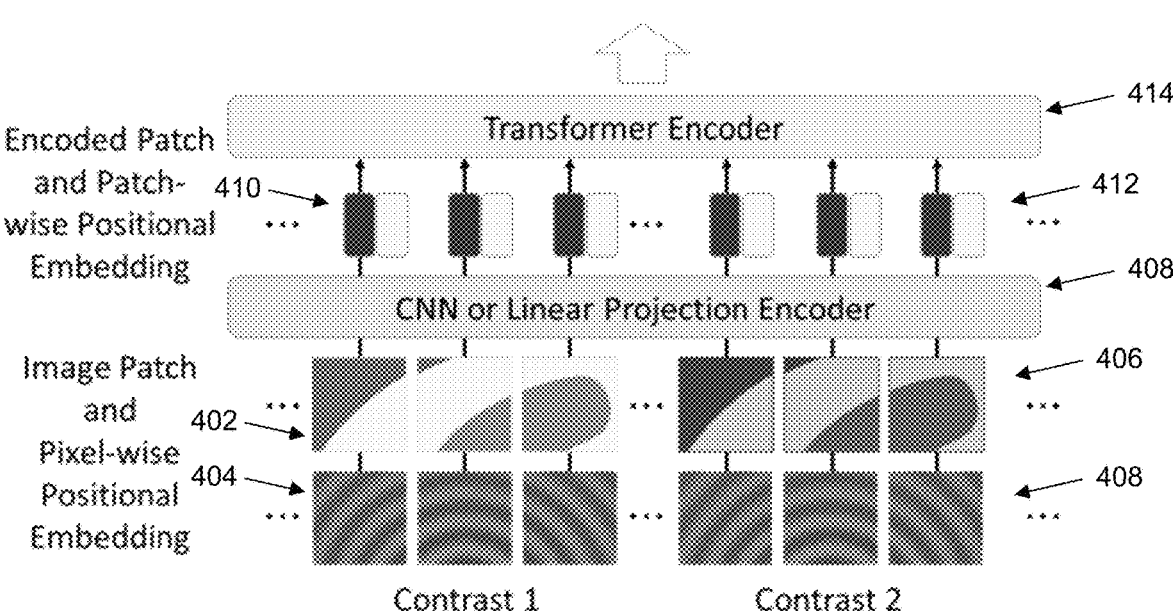
FIG. 4 shows a workflow for performing a medical imaging analysis task by separately encoding each patch extracted from the input medical images with its corresponding patch extracted from the pixelwise positional embedding images, in accordance with one or more embodiments.

In one embodiment, for example where the one or more input medical images is a plurality of input medical images (e.g., in different imaging modalities or from multiple MR sequences), if the input medical images have different spatial relationships with different spatial coordinate systems, each patch extracted from the plurality of input medical images are combined with its corresponding patch extracted from the pixelwise positional embedding images and the combined patches are separately encoded by the encoder. FIG. 4 shows a workflow 400 for performing a medical imaging analysis task by separately encoding each patch extracted from the input medical images with its corresponding patch extracted from the pixelwise positional embedding images, in accordance with one or more embodiments. Patches 402 extracted from contrast 1 image and patches 406 extracted from a contrast 2 image have a different spatial relationship. Patches 402 and 406 are respectively combined with their corresponding patches 404 and 408 extracted from pixelwise positional embedding images and the combined patches are encoded by encoder 408 to generate pixelwise positionally encoded features 410 and 412. FIG. 4 will be described in further detail below.

Figure 5:
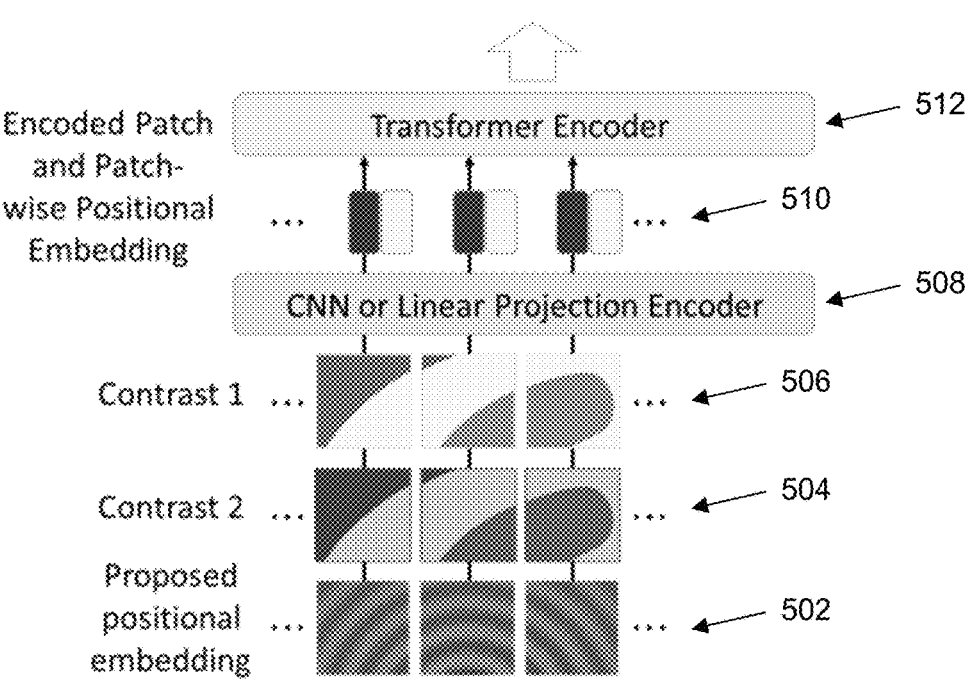
FIG. 5 shows a workflow for performing a medical imaging analysis task by encoding corresponding patches extracted from the input medica images and from the pixelwise positional embedding image, in accordance with one or more embodiments.

In one embodiment, for example where the one or more input medical images is a plurality of input medical images, if the input medical images have the same spatial relationship in the same spatial coordinate system, the pixelwise positional embedding images are the same and thus there is a single pixelwise positional embedding image. Corresponding patches extracted from each of the plurality of input medical images and from the pixelwise positional embedding image are combined and each of the combined patches are separately encoded by the encoder. FIG. 5 shows a workflow 500 for performing a medical imaging analysis task by encoding corresponding patches extracted from the input medica images and from the single pixelwise positional embedding image, in accordance with one or more embodiments. Patches 506 extracted from contrast 1 image and patches 504 extracted from a contrast 2 image have a same spatial relationship. Corresponding patches 506 and 504 and patches 502 extracted from pixelwise positional embedding image are combined and the combined patches are separately encoded by encoder 508 to generate pixelwise positionally encoded features 510. FIG. 5 will be described in further detail below.

At step 110 of FIG. 1, a medical imaging analysis task is performed using a machine learning based network based on the pixelwise positionally encoded features. The medical imaging analysis task may be any medical imaging analysis task, such as, e.g., detection, classification, segmentation, etc.

In one embodiment, the machine learning based network is a vision transformer network. However, the machine learning based network may be any suitable machine learning based network. The machine learning based network receives as input the pixelwise positionally encoded features and generates as output results of the medical imaging task. The machine learning based network utilizes the positional information encoded in the pixelwise positionally encoded features for performing the medical imaging analysis task. The machine learning based network is trained during a prior offline or training stage. Once trained, the machine learning based network is applied during an online or inference stage, e.g., to perform step 110 of FIG. 1. In one example, the machine learning based network is transformer encoder 414 of FIG. 4 or transformer encoder 512 of FIG. 5.

At step 112 of FIG. 1, results of the medical imaging analysis task are output. For example, the results of the medical imaging analysis task can be output by displaying the results of the medical imaging analysis task on a display device of a computer system, storing the results of the medical imaging analysis task on a memory or storage of a computer system, or by transmitting the results of the medical imaging analysis task to a remote computer system.

In one embodiment, at step 108 of FIG. 1, the patches extracted from the one or more input medical images are additionally encoded with patch-wise positionally embedded features to generate patch-wise and pixelwise positionally encoded features. The patch-wise positionally embedded features may be generated, e.g., according to known techniques. The medical imaging analysis task is performed at step 110 of FIG. 1 based on the patch-wise and pixelwise positionally encoded features.

Advantageously, the pixelwise positionally embeddings in accordance with embodiments described herein provide for input flexibility. With the pixelwise positionally embeddings, the vision transformer has the ability to receive input images acquired with different spatial relationships between voxel and spatial coordinate systems without resampling and without losing the spatial relationships. In this way, resampling, which can cause information loss and compromise the network's performance, can be avoided. Further, the pixelwise positionally embeddings provides for pixel level position relation. The pixelwise positionally embedding values depend on the position of each pixel in the reference coordinate system. The difference of two input images' pixelwise positionally embeddings can reflect the difference of their pixel grids. Thus, the pixelwise positionally embeddings can provide the vision transformer with the relative position information of each patch's pixel grid in the 3D space. In this way, the vision transformer trained with the pixelwise positionally embeddings can potentially learn the position relation of each patch down to the pixel level to accurately extract and align information from each patch and achieve better performance.

Embodiments described herein were experimentally validated. Performance improvement attributable to the pixelwise positional embeddings was demonstrated on the medical imaging analysis task of acute/subacute brain infarction segmentation with a dataset of 1142, 133, and 143 subjects in the training, validation, and testing splits. FIG. 6 shows a table 600 comparing performance of embodiments described herein with conventional approaches. Table 600 shows the proposed positional embedding (representing the pixelwise positional embeddings in accordance with embodiments described herein) outperform both UNETR (UNet Transformer) and Swin UNETR's original positional embedding (representing conventional patch-wise positional embedding).

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based model can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 7:
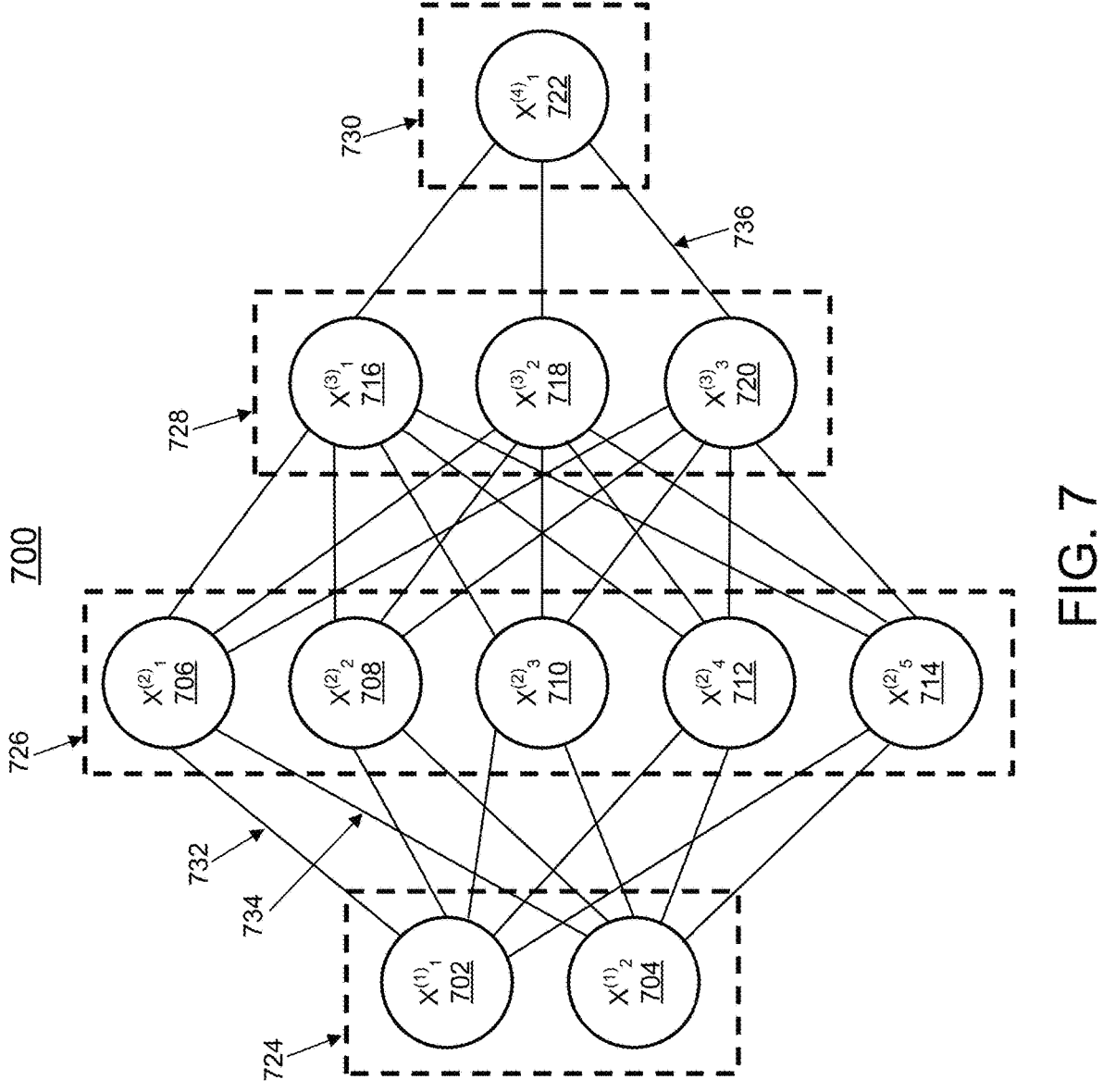
FIG. 7 shows an exemplary artificial neural network that may be used to implement one or more embodiments.

FIG. 7 shows an embodiment of an artificial neural network 700, in accordance with one or more embodiments. Alternative terms for "artificial neural network" are "neural network", "artificial neural net" or "neural net". Machine learning networks described herein, such as, e.g., the machine learning based encoder network which may be utilized at step 108 or the machine learning based network utilized at step 110 of FIG. 1, the CNN encoder 408 of FIG. 4, or the CNN encoder 508 of FIG. 5, may be implemented using artificial neural network 700.

The artificial neural network 700 comprises nodes 702-722 and edges 732, 734, . . . , 736, wherein each edge 732, 734, . . . , 736 is a directed connection from a first node 702-722 to a second node 702-722. In general, the first node 702-722 and the second node 702-722 are different nodes 702-722, it is also possible that the first node 702-722 and the second node 702-722 are identical. For example, in FIG. 7, the edge 732 is a directed connection from the node 702 to the node 706, and the edge 734 is a directed connection from the node 704 to the node 706. An edge 732, 734, . . . , 736 from a first node 702-722 to a second node 702-722 is also denoted as "ingoing edge" for the second node 702-722 and as "outgoing edge" for the first node 702-722.

In this embodiment, the nodes 702-722 of the artificial neural network 700 can be arranged in layers 724-730, wherein the layers can comprise an intrinsic order introduced by the edges 732, 734, . . . , 736 between the nodes 702-722. In particular, edges 732, 734, . . . , 736 can exist only between neighboring layers of nodes. In the embodiment shown in FIG. 7, there is an input layer 724 comprising only nodes 702 and 704 without an incoming edge, an output layer 730 comprising only node 722 without outgoing edges, and hidden layers 726, 728 in-between the input layer 724 and the output layer 730. In general, the number of hidden layers 726, 728 can be chosen arbitrarily. The number of nodes 702 and 704 within the input layer 724 usually relates to the number of input values of the neural network 700, and the number of nodes 722 within the output layer 730 usually relates to the number of output values of the neural network 700.

In particular, a (real) number can be assigned as a value to every node 702-722 of the neural network 700. Here, $x^{(n)}_i$ denotes the value of the i-th node 702-722 of the n-th layer 724-730. The values of the nodes 702-722 of the input layer 724 are equivalent to the input values of the neural network 700, the value of the node 722 of the output layer 730 is equivalent to the output value of the neural network 700. Furthermore, each edge 732, 734, . . . , 736 can comprise a weight being a real number, in particular, the weight is a real number within the interval [−1, 1] or within the interval [0, 1]. Here, $w^{(m,n)}_{i,j}$ denotes the weight of the edge between the i-th node 702-722 of the m-th layer 724-730 and the j-th node 702-722 of the n-th layer 724-730. Furthermore, the abbreviation $w^{(n)}_{i,j}$ is defined for the weight $w^{(n,n+1)}_{i,j}$.

In particular, to calculate the output values of the neural network 700, the input values are propagated through the neural network. In particular, the values of the nodes 702-722 of the (n+1)-th layer 724-730 can be calculated based on the values of the nodes 702-722 of the n-th layer 724-730 by $$x_j^{(n+1)} = f\left(\sum_i x_i^{(n)} \cdot w_{i,j}^{(n)}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 724 are given by the input of the neural network 700, wherein values of the first hidden layer 726 can be calculated based on the values of the input layer 724 of the neural network, wherein values of the second hidden layer 728 can be calculated based in the values of the first hidden layer 726, etc.

In order to set the values $w^{(m,n)}_{i,j}$ for the edges, the neural network 700 has to be trained using training data. In particular, training data comprises training input data and training output data (denoted as $t_i$). For a training step, the neural network 700 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 700 (backpropagation algorithm). In particular, the weights are changed according to $$w_{i,j}^{\prime(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = \left(\sum_k \delta_k^{(n+1)} \cdot w_{j,k}^{(n+1)}\right) \cdot f'\left(\sum_i x_i^{(n)} \cdot w_{i,j}^{(n)}\right)$$

based on $\delta^{(n+1)}_j$, if the (n+1)-th layer is not the output layer, and $$\delta_j^{(n)} = \left(x_k^{(n+1)} - t_j^{(n+1)}\right) \cdot f'\left(\sum_i x_i^{(n)} \cdot w_{i,j}^{(n)}\right)$$

if the (n+1)-th layer is the output layer 730, wherein f' is the first derivative of the activation function, and $y^{(n+1)}_j$ is the comparison training value for the j-th node of the output layer 730.

Figure 8:
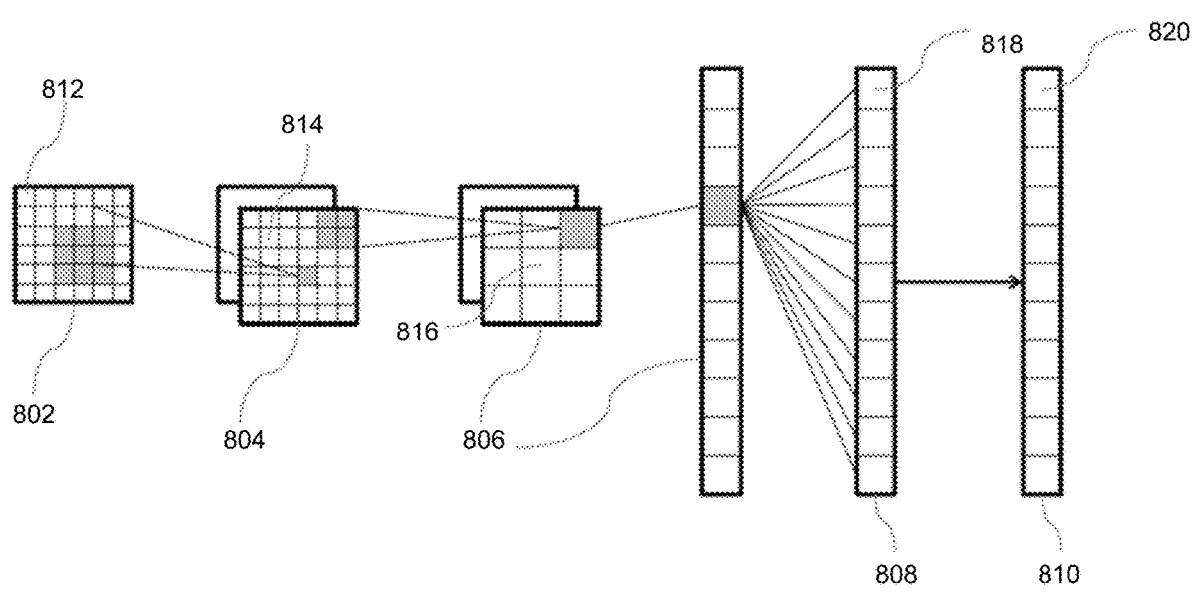
FIG. 8 shows a convolutional neural network that may be used to implement one or more embodiments.

FIG. 8 shows a convolutional neural network 800, in accordance with one or more embodiments. Machine learning networks described herein, such as, e.g., the machine learning based encoder network which may be utilized at step 108 or the machine learning based network utilized at step 110 of FIG. 1, the CNN encoder 408 of FIG. 4, or the CNN encoder 508 of FIG. 5, may be implemented using convolutional neural network 800.

In the embodiment shown in FIG. 8, the convolutional neural network comprises 800 an input layer 802, a convolutional layer 804, a pooling layer 806, a fully connected layer 808, and an output layer 810. Alternatively, the convolutional neural network 800 can comprise several convolutional layers 804, several pooling layers 806, and several fully connected layers 808, as well as other types of layers. The order of the layers can be chosen arbitrarily, usually fully connected layers 808 are used as the last layers before the output layer 810.

In particular, within a convolutional neural network 800, the nodes 812-820 of one layer 802-810 can be considered to be arranged as a d-dimensional matrix or as a d-dimensional image. In particular, in the two-dimensional case the value of the node 812-820 indexed with i and j in the n-th layer 802-810 can be denoted as $x^{(n)}_{[i,j]}$. However, the arrangement of the nodes 812-820 of one layer 802-810 does not have an effect on the calculations executed within the convolutional neural network 800 as such, since these are given solely by the structure and the weights of the edges.

In particular, a convolutional layer 804 is characterized by the structure and the weights of the incoming edges forming a convolution operation based on a certain number of kernels. In particular, the structure and the weights of the incoming edges are chosen such that the values $x^{(n)}_k$ of the nodes 814 of the convolutional layer 804 are calculated as a convolution $x^{(n)}_k = K_k * x^{(n-1)}$ based on the values $x^{(n-1)}$ of the nodes 812 of the preceding layer 802, where the convolution * is defined in the two-dimensional case as $$x_k^{(n)}[i, j] = \left(K_k * x^{(n-1)}\right)[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 812-818 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 812-820 in the respective layer 802-810. In particular, for a convolutional layer 804, the number of nodes 814 in the convolutional layer is equivalent to the number of nodes 812 in the preceding layer 802 multiplied with the number of kernels.

If the nodes 812 of the preceding layer 802 are arranged as a d-dimensional matrix, using a plurality of kernels can be interpreted as adding a further dimension (denoted as "depth" dimension), so that the nodes 814 of the convolutional layer 804 are arranged as a (d+1)-dimensional matrix. If the nodes 812 of the preceding layer 802 are already arranged as a (d+1)-dimensional matrix comprising a depth dimension, using a plurality of kernels can be interpreted as expanding along the depth dimension, so that the nodes 814 of the convolutional layer 804 are arranged also as a (d+1)-dimensional matrix, wherein the size of the (d+1)-dimensional matrix with respect to the depth dimension is by a factor of the number of kernels larger than in the preceding layer 802.

The advantage of using convolutional layers 804 is that spatially local correlation of the input data can exploited by enforcing a local connectivity pattern between nodes of adjacent layers, in particular by each node being connected to only a small region of the nodes of the preceding layer.

In embodiment shown in FIG. 8, the input layer 802 comprises 36 nodes 812, arranged as a two-dimensional 6×6 matrix. The convolutional layer 804 comprises 72 nodes 814, arranged as two two-dimensional 6×6 matrices, each of the two matrices being the result of a convolution of the values of the input layer with a kernel. Equivalently, the nodes 814 of the convolutional layer 804 can be interpreted as arranges as a three-dimensional 6×6×2 matrix, wherein the last dimension is the depth dimension.

A pooling layer 806 can be characterized by the structure and the weights of the incoming edges and the activation function of its nodes 816 forming a pooling operation based on a non-linear pooling function f. For example, in the two dimensional case the values $x^{(n)}$ of the nodes 816 of the pooling layer 806 can be calculated based on the values $x^{(n-1)}$ of the nodes 814 of the preceding layer 804 as $$x^{(n)}[i, j] = f\left(x^{(n-1)}[id_1, jd_2], \dots, x^{(n-1)}[id_1 + d_1 - 1, jd_2 + d_2 - 1]\right)$$

In other words, by using a pooling layer 806, the number of nodes 814, 816 can be reduced, by replacing a number $d1 \cdot d2$ of neighboring nodes 814 in the preceding layer 804 with a single node 816 being calculated as a function of the values of said number of neighboring nodes in the pooling layer. In particular, the pooling function f can be the max-function, the average or the L2-Norm. In particular, for a pooling layer 806 the weights of the incoming edges are fixed and are not modified by training.

The advantage of using a pooling layer 806 is that the number of nodes 814, 816 and the number of parameters is reduced. This leads to the amount of computation in the network being reduced and to a control of overfitting.

In the embodiment shown in FIG. 8, the pooling layer 806 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 808 can be characterized by the fact that a majority, in particular, all edges between nodes 816 of the previous layer 806 and the nodes 818 of the fully-connected layer 808 are present, and wherein the weight of each of the edges can be adjusted individually.

In this embodiment, the nodes 816 of the preceding layer 806 of the fully-connected layer 808 are displayed both as two-dimensional matrices, and additionally as non-related nodes (indicated as a line of nodes, wherein the number of nodes was reduced for a better presentability). In this embodiment, the number of nodes 818 in the fully connected layer 808 is equal to the number of nodes 816 in the preceding layer 806. Alternatively, the number of nodes 816, 818 can differ.

Furthermore, in this embodiment, the values of the nodes 820 of the output layer 810 are determined by applying the Softmax function onto the values of the nodes 818 of the preceding layer 808. By applying the Softmax function, the sum the values of all nodes 820 of the output layer 810 is 1, and all values of all nodes 820 of the output layer are real numbers between 0 and 1.

A convolutional neural network 800 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 800 can be trained based on the backpropagation algorithm. For preventing overfitting, methods of regularization can be used, e.g. dropout of nodes 812-820, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 3-5. Certain steps or functions of the methods and workflows described herein, including one or more of the steps or functions of FIG. 1 or 3-5, may be performed by a server or by another processor in a network-based cloud-computing system. Certain steps or functions of the methods and workflows described herein, including one or more of the steps of FIG. 1 or 3-5, may be performed by a client computer in a network-based cloud computing system. The steps or functions of the methods and workflows described herein, including one or more of the steps of FIG. 1 or 3-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 3-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIG. 1 or 3-5 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIG. 1 or 3-5. Accordingly, by executing the computer program instructions, the processor 904 executes the method and workflow steps or functions of FIG. 1 or 3-5. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving one or more input medical images; generating one or more pixelwise positional embedding images for the one or more input medical images using a spatially varying function; extracting patches from the one or more input medical images and the one or more pixelwise positional embedding images; encoding the patches extracted from the one or more input medical images with corresponding ones of the patches extracted from the one or more pixelwise positional embedding images into pixelwise positionally encoded features; performing a medical imaging analysis task using a machine learning based network based on the pixelwise positionally encoded features; and outputting results of the medical imaging analysis task.

Illustrative embodiment 2. The computer-implemented method of illustrative embodiment 1, wherein generating one or more pixelwise positional embedding images for the one or more input medical images using a spatially varying function comprises: sampling a spatially varying function at a location of each pixel of the one or more input medical images.

Illustrative embodiment 3. The computer-implemented method according to one of the preceding embodiments, wherein the spatially varying function is a sinusoidal function.

Illustrative embodiment 4. The computer-implemented method according to one of the preceding embodiments, wherein the spatially varying function is in reference coordinate system defined relative to the one or more input medical images.

Illustrative embodiment 5. The computer-implemented method according to one of the preceding embodiments, wherein the reference coordinate system comprises a physical coordinate system of an image acquisition device that acquired the one or more input medical images.

Illustrative embodiment 6. The computer-implemented method according to one of the preceding embodiments, wherein the one or more input medical images comprises a plurality of input medical images and the one or more pixelwise positional embedding images comprises a plurality of pixelwise positional embedding images, and encoding the patches extracted from the one or more input medical images with corresponding ones of the patches extracted from the one or more pixelwise positional embedding images into pixelwise positionally encoded features comprises: combining each patch extracted from the plurality of input medical images with its corresponding patch extracted from the plurality of pixelwise positional embedding images; and separately encoding the combined patches.

Illustrative embodiment 7. The computer-implemented method according to one of the preceding embodiments, wherein the one or more input medical images comprises a plurality of input medical images and the one or more pixelwise positional embedding images comprises a single pixelwise positional embedding image, and encoding the patches extracted from the one or more input medical images with corresponding ones of the patches extracted from the one or more pixelwise positional embedding images into pixelwise positionally encoded features comprises: combining corresponding patches extracted from each of the plurality of input medical images and from the single pixelwise positional embedding image; and separately encoding the combined patches.

Illustrative embodiment 8. The computer-implemented method according to one of the preceding embodiments, wherein: encoding the patches extracted from the one or more input medical images with corresponding ones of the patches extracted from the one or more pixelwise positional embedding images into pixelwise positionally encoded features comprises encoding the patches extracted from the one or more input medical images with patch-wise positionally embedded features to generate patch-wise and pixelwise positionally encoded features; and performing a medical imaging analysis task using a machine learning based network based on the pixelwise positionally encoded features comprises performing the medical imaging analysis task based on the patch-wise and pixelwise positionally encoded features.

Illustrative embodiment 9. The computer-implemented method according to one of the preceding embodiments, wherein the machine learning based network is a vision transformer network.

Illustrative embodiment 10. An apparatus comprising: means for receiving one or more input medical images; means for generating one or more pixelwise positional embedding images for the one or more input medical images using a spatially varying function; means for extracting patches from the one or more input medical images and the one or more pixelwise positional embedding images; means for encoding the patches extracted from the one or more input medical images with corresponding ones of the patches extracted from the one or more pixelwise positional embedding images into pixelwise positionally encoded features; means for performing a medical imaging analysis task using a machine learning based network based on the pixelwise positionally encoded features; and means for outputting results of the medical imaging analysis task.

Illustrative embodiment 11. The apparatus of illustrative embodiment 10, wherein the means for generating one or more pixelwise positional embedding images for the one or more input medical images using a spatially varying function comprises: means for sampling a spatially varying function at a location of each pixel of the one or more input medical images.

Illustrative embodiment 12. The apparatus of any one of illustrative embodiments 10-11, wherein the spatially varying function is a sinusoidal function.

Illustrative embodiment 13. The apparatus of any one of illustrative embodiments 10-12, wherein the spatially varying function is in reference coordinate system defined relative to the one or more input medical images.

Illustrative embodiment 14. The apparatus of any one of illustrative embodiments 10-13, wherein the reference coordinate system comprises a physical coordinate system of an image acquisition device that acquired the one or more input medical images.

Illustrative embodiment 15. A non-transitory computer readable medium storing computer program instructions, the computer program instructions when executed by a processor cause the processor to perform operations comprising: receiving one or more input medical images; generating one or more pixelwise positional embedding images for the one or more input medical images using a spatially varying function; extracting patches from the one or more input medical images and the one or more pixelwise positional embedding images; encoding the patches extracted from the one or more input medical images with corresponding ones of the patches extracted from the one or more pixelwise positional embedding images into pixelwise positionally encoded features; performing a medical imaging analysis task using a machine learning based network based on the pixelwise positionally encoded features; and outputting results of the medical imaging analysis task.

Illustrative embodiment 16. The non-transitory computer readable medium of illustrative embodiment 15, wherein generating one or more pixelwise positional embedding images for the one or more input medical images using a spatially varying function comprises: sampling a spatially varying function at a location of each pixel of the one or more input medical images.

Illustrative embodiment 17. The non-transitory computer readable medium of any one of illustrative embodiments 15-16, wherein the one or more input medical images comprises a plurality of input medical images and the one or more pixelwise positional embedding images comprises a plurality of pixelwise positional embedding images, and encoding the patches extracted from the one or more input medical images with corresponding ones of the patches extracted from the one or more pixelwise positional embedding images into pixelwise positionally encoded features comprises: combining each patch extracted from the plurality of input medical images with its corresponding patch extracted from the plurality of pixelwise positional embedding images; and separately encoding the combined patches.

Illustrative embodiment 18. The non-transitory computer readable medium of any one of illustrative embodiments 15-17, wherein the one or more input medical images comprises a plurality of input medical images and the one or more pixelwise positional embedding images comprises a single pixelwise positional embedding image, and encoding the patches extracted from the one or more input medical images with corresponding ones of the patches extracted from the one or more pixelwise positional embedding images into pixelwise positionally encoded features comprises: combining corresponding patches extracted from each of the plurality of input medical images and from the single pixelwise positional embedding image; and separately encoding the combined patches.

Illustrative embodiment 19. The non-transitory computer readable medium of any one of illustrative embodiments 15-18, wherein: encoding the patches extracted from the one or more input medical images with corresponding ones of the patches extracted from the one or more pixelwise positional embedding images into pixelwise positionally encoded features comprises encoding the patches extracted from the one or more input medical images with patch-wise positionally embedded features to generate patch-wise and pixelwise positionally encoded features; and performing a medical imaging analysis task using a machine learning based network based on the pixelwise positionally encoded features comprises performing the medical imaging analysis task based on the patch-wise and pixelwise positionally encoded features.

Illustrative embodiment 20. The non-transitory computer readable medium of any one of illustrative embodiments 15-19, wherein the machine learning based network is a vision transformer network.

The invention claimed is:

1. A computer-implemented method comprising:
receiving one or more input medical images;
generating one or more pixelwise positional embedding images for the one or more input medical images using a spatially varying function;
extracting patches from the one or more input medical images and the one or more pixelwise positional embedding images;
encoding the patches extracted from the one or more input medical images with corresponding ones of the patches extracted from the one or more pixelwise positional embedding images into pixelwise positionally encoded features by:
combining each patch extracted from the one or more input medical images with its corresponding patch extracted from the one or more pixelwise positional embedding images, and
separately encoding the combined patches;
performing a medical imaging analysis task using a machine learning based network based on the pixelwise positionally encoded features; and
outputting results of the medical imaging analysis task.

2. The computer-implemented method of claim 1, wherein generating one or more pixelwise positional embedding images for the one or more input medical images using a spatially varying function comprises:
sampling a spatially varying function at a location of each pixel of the one or more input medical images.

3. The computer-implemented method of claim 1, wherein the spatially varying function is a sinusoidal function.

4. The computer-implemented method of claim 1, wherein the spatially varying function is in reference coordinate system defined relative to the one or more input medical images.

5. The computer-implemented method of claim 4, wherein the reference coordinate system comprises a physical coordinate system of an image acquisition device that acquired the one or more input medical images.

6. The computer-implemented method of claim 1, wherein the one or more input medical images comprises a plurality of input medical images and the one or more pixelwise positional embedding images comprises a plurality of pixelwise positional embedding images.

7. The computer-implemented method of claim 1, wherein the one or more input medical images comprises a plurality of input medical images and the one or more pixelwise positional embedding images comprises a single pixelwise positional embedding image.

8. The computer-implemented method of claim 1, wherein:

encoding the patches extracted from the one or more input medical images with corresponding ones of the patches extracted from the one or more pixelwise positional embedding images into pixelwise positionally encoded features comprises encoding the patches extracted from the one or more input medical images with patch-wise positionally embedded features to generate patch-wise and pixelwise positionally encoded features; and performing a medical imaging analysis task using a machine learning based network based on the pixelwise positionally encoded features comprises performing the medical imaging analysis task based on the patch-wise and pixelwise positionally encoded features.

9. The computer-implemented method of claim 1, wherein the machine learning based network is a vision transformer network.

10. An apparatus comprising:

means for receiving one or more input medical images;

means for generating one or more pixelwise positional embedding images for the one or more input medical images using a spatially varying function;

means for extracting patches from the one or more input medical images and the one or more pixelwise positional embedding images;

means for encoding the patches extracted from the one or more input medical images with corresponding ones of the patches extracted from the one or more pixelwise positional embedding images into pixelwise positionally encoded features by:

combining each patch extracted from the one or more input medical images with its corresponding patch extracted from the one or more pixelwise positional embedding images, and separately encoding the combined patches;

means for performing a medical imaging analysis task using a machine learning based network based on the pixelwise positionally encoded features; and means for outputting results of the medical imaging analysis task.

11. The apparatus of claim 10, wherein the means for generating one or more pixelwise positional embedding images for the one or more input medical images using a spatially varying function comprises:

means for sampling a spatially varying function at a location of each pixel of the one or more input medical images.

12. The apparatus of claim 10, wherein the spatially varying function is a sinusoidal function.

13. The apparatus of claim 10, wherein the spatially varying function is in reference coordinate system defined relative to the one or more input medical images.

14. The apparatus of claim 13, wherein the reference coordinate system comprises a physical coordinate system of an image acquisition device that acquired the one or more input medical images.

15. A non-transitory computer readable medium storing computer program instructions, the computer program instructions when executed by a processor cause the processor to perform operations comprising:

receiving one or more input medical images;

generating one or more pixelwise positional embedding images for the one or more input medical images using a spatially varying function;

extracting patches from the one or more input medical images and the one or more pixelwise positional embedding images;

encoding the patches extracted from the one or more input medical images with corresponding ones of the patches extracted from the one or more pixelwise positional embedding images into pixelwise positionally encoded features by:

combining each patch extracted from the one or more input medical images with its corresponding patch extracted from the one or more pixelwise positional embedding images, and separately encoding the combined patches;

performing a medical imaging analysis task using a machine learning based network based on the pixelwise positionally encoded features; and outputting results of the medical imaging analysis task.

16. The non-transitory computer readable medium of claim 15, wherein generating one or more pixelwise positional embedding images for the one or more input medical images using a spatially varying function comprises:

sampling a spatially varying function at a location of each pixel of the one or more input medical images.

17. The non-transitory computer readable medium of claim 15, wherein the one or more input medical images comprises a plurality of input medical images and the one or more pixelwise positional embedding images comprises a plurality of pixelwise positional embedding images.

18. The non-transitory computer readable medium of claim 15, wherein the one or more input medical images comprises a plurality of input medical images and the one or more pixelwise positional embedding images comprises a single pixelwise positional embedding image.

19. The non-transitory computer readable medium of claim 15, wherein:

encoding the patches extracted from the one or more input medical images with corresponding ones of the patches extracted from the one or more pixelwise positional embedding images into pixelwise positionally encoded features comprises encoding the patches extracted from the one or more input medical images with patch-wise positionally embedded features to generate patch-wise and pixelwise positionally encoded features; and performing a medical imaging analysis task using a machine learning based network based on the pixelwise positionally encoded features comprises performing the medical imaging analysis task based on the patch-wise and pixelwise positionally encoded features.

20. The non-transitory computer readable medium of claim 15, wherein the machine learning based network is a vision transformer network.

* * * * *